United States Patent [19]

Grundmann et al.

[11] Patent Number: 5,317,094

[45] Date of Patent: *May 31, 1994

[54] PROTEIN PP 15 PREPRARED BY GENETIC MANIPULATION

[75] Inventors: Ulrich Grundmann, Lahntal-Grossfelden; Karl-Josef Abel; Eugen Amann, both of Marburg, all of Fed. Rep. of Germany

[73] Assignee: Behringwerke Aktiengesellschaft, Marburg/Lahn, Fed. Rep. of Germany

[*] Notice: The portion of the term of this patent subsequent to Feb. 23, 2010 has been disclaimed.

[21] Appl. No.: 928,039

[22] Filed: Aug. 11, 1992

Related U.S. Application Data

[60] Division of Ser. No. 709,790, Jun. 3, 1991, Pat. No. 5,188,933, which is a continuation of Ser. No. 324,068, Mar. 16, 1989, abandoned.

[30] Foreign Application Priority Data

Mar. 18, 1988 [DE] Fed. Rep. of Germany ........ 3809119

[51] Int. Cl.$^5$ ..................... C07H 21/02; C07H 21/04; C12N 15/70; C12N 15/74
[52] U.S. Cl. ........................................ 536/23.5; 435/6; 435/320.1; 536/23.1
[58] Field of Search ..................... 536/27; 435/6, 320.1

[56] References Cited

PUBLICATIONS

Maniatis et al., Molecular CLoning (1982) Cold Spring Harbor Press; CSH, N.Y. pp. 388–389.
Hames et al., Nucleic Acid Hyhidization, (1985) IRL Press, Wash. D.C. pp. 8–9.
Bloomfield et al., Physical Chemistry of Nucleic Acids (1974), Harper & Row NY, N.Y. pp. 328–332.
Barker et al. Eur J. Biochem 127:449–457 1982.
Grundmann et al. Nuc Acids Res 16(10):4721 (1988).
R. Lathe, J. Mol. Biol., 183 (1985) pp. 1–12.
Chirgwin et al., Biochemistry, 18 (1979) pp. 5294–5299.
Aviv et al. Proc. Natl. Acad. Sci. USA, 69, No. 6 (1979) pp. 1408–1412.
Gubler et al., Gene 25 (1983) pp. 263–269.
T. Maniatis et al., Molecular Cloning, A Laboratory Manual, Cold Spring Harbour (1982), pp. 242–246.
Enquist et al., Methods in Enzymology, 68 (1979) pp. 281–298.

Primary Examiner—Mindy B. Fleisher
Attorney, Agent, or Firm—Finnegan, Henderson, Farabow, Garrett & Dunner

[57] ABSTRACT

Specific fragments of the protein PP15 were prepared by enzyme cleavage. Using statistical data, specific oligonucleotides were selected from the oligonucleotides coding for the specific PP15 fragments. These oligonucleotides were then used as probes to successfully screen a cDNA bank of mature human placenta and isolate the complete cDNA of PP15. The cDNA was sequenced and characterized. This cDNA can be used to prepare PP15 protein in prokaryotic or eukaryotic cells.

3 Claims, 3 Drawing Sheets

```
         10                      30                             50
GGAAGGGACAGTCGGCCGGCCGCAGACCGCGGCTGGGTTGCCGCTGCCGCTGCCATCGTGCC
           70                       90                      110
AGCCCCTCGGTCTCCGGTGAGGCCGGGTGACGCTCCAGAATGGGAGACAAGCCAATTTGG
                                                  M  G  D  K  P  I  W
          130                     150                     170
GAGCAGATTGGATCCAGCTTCATTCAACATTACTACCAGTTATTTGATAATGATAGAACC
 E  Q  I  G  S  S  F  I  Q  H  Y  Y  Q  L  F  D  N  D  R  T
          190                     210                     230
CAACTAGGCGCAATTTACATTGACGCGTCATGCCTTACGTGGGAAGGACAACAGTTCCAG
 Q  L  G  A  I  Y  I  D  A  S  C  L  T  W  E  G  Q  Q  F  Q
          250                     270                     290
GGGAAAGCTGCCATTGTGGAGAAGTTGTCTAGCCTTCCGTTCCAGAAAATTCAGCACAGC
 G  K  A  A  I  V  E  K  L  S  S  L  P  F  Q  K  I  Q  H  S
          310                     330                     350
ATCACCGCGCAGGACCATCAGCCCACTCCAGATAGCTGCATCATCAGCATGGTTGTGGGC
 I  T  A  Q  D  H  Q  P  T  P  D  S  C  I  I  S  M  V  V  G
```

FIG. 2

CAGCTTAAGGGCGGATGAAGACCCCATCATGGGGTTCCACCAGATGTTCCTATTAAAGAAC
          370                390                 410
 Q   L   K   A   D   E   D   P   I   M   G   F   H   Q   M   F   L   L   K   N

ATCAACGATGCTTGGGTTTGCACCAATGACATGTTCAGGCTCGCCCTGCACAACTTTGGC
          430                450                 470
 I   N   D   A   W   V   C   T   N   D   M   F   R   L   A   L   H   N   F   G

TGACCTCCTCTCAGCTAGGCACTCACGCTGTTTCCTCCCTCCTCTTCCCAATACTAT
          490                510                 530
                    550                570                590

TCCCACTCCTCCAGATGCTCCAAATATCATGAGCACAAATGAGCAGGCCGCGGTGGGAGTG
          610                630                650

GGCGCAGTGCGCTGCTGCCACTGAGGTGTTGTGCATGATGTTTGGATGCTAGACTAGTTG
          670                690                710

CATCTGACGGGAGAAGTTTGTGTTGTACCAGCGCATGCCTTGGAAAGACTTAAGTAATGC
          730                750                770

AAAAGGTTGTCCTTTTTTTTTTTTTTAATCTACTGACAAGTTGCTCTAGTAA
          790                810                830

CCCAAAGAAGTGAAGGAGAAAGCAGCTGCCTCACCGCCCAGACATTGATTGTTCAGATG
          850                870                890

TTTCAATGCCTCATGATACAATAAAACCACAAAATTTCTTAACAAAAAAAA

FIG. 2 cont.

PROTEIN PP 15 PREPRARED BY GENETIC MANIPULATION

This is a division of application Ser. No. 07/709,790, filed Jun. 3, 1991, now U.S. Pat. No. 5,188,933 which is a continuation of application Ser. No. 07/324,068 filed Mar. 16, 1989.

DESCRIPTION

The protein PP 15, which has an immunosuppresant action, is described in DE-A 29 52 792 (U.S. Pat. No. 4,348,316) with the following parameters:

a) a carbohydrate content of 3.35±0.9%, composed of 2.8±0.5% hexoses, 0.3±0.2% hexosamines, 0.05±0.05% fucose and 0.20±0.15% neuraminic acid;

b) a sedimentation coefficient $S_{20,w}O$ of 2.9±0.2 S;

c) a molecular weight determined in the ultracentrifuge of 30,700±3,200 (dimer);

d) an extinction coefficient $E^{1\%}_{1\ cm}$ (280 nm) of 14.2±1.0, and e) an electrophoretic mobility in the region of that of albumin, as well as f) an isoelectric point of 4.4±0.1;

g) the amino acid composition

| Amino acid | Residues per 100 residues (mol-%) | Coefficient of variation (%) |
|---|---|---|
| Lysine | 4.74 | 3.30 |
| Histidine | 3.81 | 5.43 |
| Arginine | 1.62 | 3.43 |
| Aspartic acid | 13.39 | 5.08 |
| Threonine | 3.85 | 5.35 |
| Serine | 6.38 | 2.81 |
| Glutamic acid | 13.43 | 5.32 |
| Proline | 4.35 | 14.25 |
| Glycine | 6.87 | 2.13 |
| Alanine | 6.51 | 8.26 |
| Cystine ½ | 2.48 | 4.55 |
| Valine | 2.29 | 15.67 |
| Methionine | 2.87 | 10.86 |
| Isoleucine | 8.39 | 8.18 |
| Leucine | 8.18 | 6.72 |
| Tyrosine | 2.09 | 8.49 |
| Phenylalanine | 6.27 | 2.27 |
| Tryptophan | 2.51 | 6.81 |

Determination of the molecular weight by SDS polyacrylamide gel electrophoresis yielded a molecular weight of about 15,000 d (monomer).

Because of the therapeutic interest aroused by the immunosuppresant properties, and of the diagnostic interest, a preparation of this protein by genetic manipulation is extremely desirable. Consequently, the invention relates to a process for the preparation of PP15 by genetic manipulation, to the mRNA necessary for this, to the cDNA obtained therefrom, to DNA structures and vectors containing this DNA in whole or in part, to cells transformed with such DNA, to the polypeptide expressed by these cells, and to the use thereof as pharmaceuticals. The invention further relates to the amino acid sequence and to part-sequences of the amino acid sequence of PP15, to specific antibodies obtained therewith, to diagnostic aids and antibody columns prepared from these antibodies, and to the polypeptide obtained using such columns. A further embodiment of the invention relates to diagnostic aids which contain, in whole or in part, RNA or DNA encoding PP15, or complementary thereto, and to diagnostic methods with which body fluids and tissue are examined using such diagnostic aids. Further aspects of the invention are explained in detail hereinafter and defined in the patent claims.

BRIEF DESCRIPTION OF THE DRAWINGS

FIG. 2 depicts the complete sequence of PP15 cDNA (coding strand).

Figure 1:
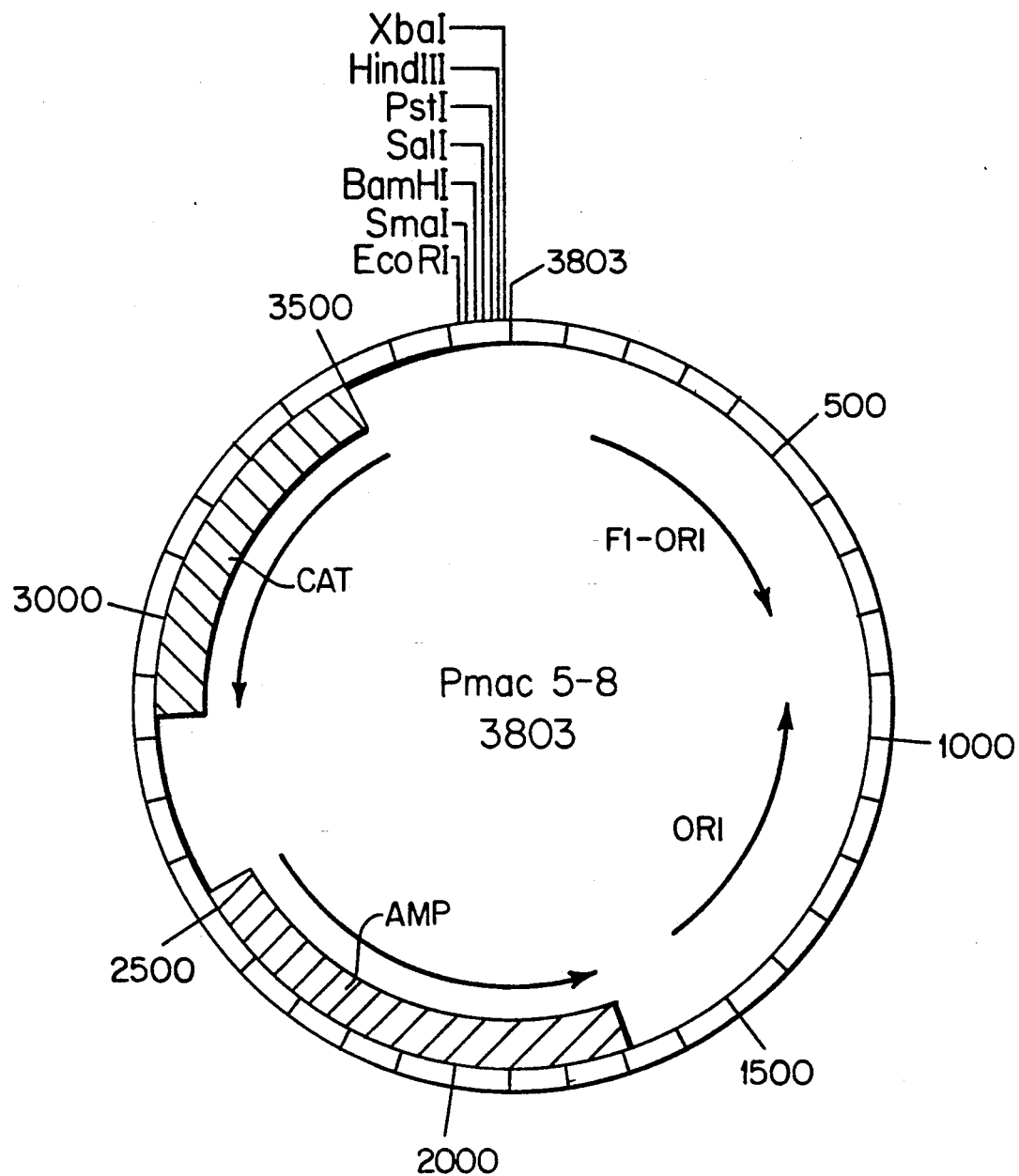
FIG. 1 depicts a map of the plasmid pMac5-8 (=pMa5-8 and pMc5-8). The following abbreviations are used: F1-ORI=origin of replication of the phage f1; ORI=origin of replication of the ColE1 type; CAT=region coding for chloramphenicol acetyltransferase; AMP=region coding for β-lactamase. pMa5-8 has an amber mutation in CAT (A at position 3409) and pMc5-8 has an amber mutation in AMP (C at position 2238).

Initially, an attempt was made, using specific antibodies against PP15, to detect in a commercially available cDNA expression bank composed of mRNA from mature human placenta (from Genofit, Heidelberg) clones which express PP15. It was known that PP15 has an immunosuppressant action, and consequently it was possible to prepare specific antibodies only unsatisfactorily, if at all, which is why specific antibodies against peptide fragments were prepared.

For this reason, the protein PP15 was broken down by cleavage with cyanogen bromide, trypsin or proteinase V8 into specific fragments which were subsequently sequenced. The following fragments were obtained:

| | | | | | | | | | | | | | | | | | | | |
|---|---|---|---|---|---|---|---|---|---|---|---|---|---|---|---|---|---|---|---|
| (A) | M | V | V | G | Q | L | K | A | D | E | D | P | I | M | G | F | H | Q | M F |
| (B) | F | R | L | A | L | H | N | F | G | | | | | | | | | | |
| (C) | V | S | V | Y | A | E | A | A | E | R | | | | | | | | | |
| (D) | L | S | S | L | P | F | Q | K | I | Q | (H) | | | | | | | | |
| (E) | F | D | N | D | R | T | Q | L | G | A | I | Y | I | D | A | S | — L | T | — E |
| (F) | L | L | K | N | I | N | D | A | W | T | | | | | | | | | |

Peptides, A, B and C were synthesized by generally known methods, and specific antibodies were raised in rabbits by customary processes. It was not possible to locate positive clones in the abovementioned cDNA expression bank, which contained $\geq 1 \times 10^6$ recombinant lambda gt11 clones. Thus, antibodies against peptide A and peptide B precipitated PP15 in control experiments, whereas antibodies against peptide C did not react. Moreover, as will be seen later, peptide C is not present in the protein sequence of PP15 subsequently derived from the cDNA sequence, so that is ought probably to be assigned to concomitant proteins of PP15.

Subsequently, statistical data by R. Lathe (J. Mol. Biol. (1985) 183, 1-12) were used to select from the oligonucleotides coding for PP15 oligopeptide A the PP15 oligonucleotide 103

5' ATGGTGGTGG GCCAGCTGAA GGCTGATGAG GACCCC, and correspondingly from the oligopeptide E the PP15 oligonucleotide 140

5' TTTGACAATG ACCGGACCCA GCTGGGCGCC ATCTACATTG ATGC and from the oligopeptide F a 64-fold degenerate PP15 oligonucleotide 139

```
5' AAAAATATTAATGATGCCTGGAC
       G   C  C    C    C
                        A
```

These oligonucleotide probes were used to screen a cDNA bank prepared from mRNA from mature human placenta. The mRNA was initially isolated from the placenta and then used to prepare the cDNA. The latter was provided with EcoRI ends and ligated into the EcoRI cleavage site of the phage vector lambda gt10. 2 clones (PP15-24 and PP15-28) which contain the complete cDNA of PP15 were detected. DNA sequencing was carried out by methods known per se; the complete sequence of PP15 cDNA (coding strand) is shown in FIG. 2. This cDNA is 894 base-pairs (bp) long, has a 99 bp untranslated sequence at the 5'-end, has an open reading frame of 381 bp, and leaves 414 bp, including eight bases of poly(A), untranslated at the 3' end.

The positions of the nucleotide probes are indicated by underlining in FIG. 2, and the amino acid sequence is additionally inserted.

It is possible according to the invention for the coding cDNA to be used, with the aid of suitable expression systems, to express PP15. Furthermore, the type of modification of PP15 can be influenced by the choice of the host. Thus, no glycoslylation takes place in bacteria, while that taking place in yeast cells differs from that in higher eukaryotic cells.

Knowing the amino acid sequence of PP15, it is possible to prepare, by conventional or genetic manipulation methods, amino acid part-sequences which can be used as antigens for the preparation of polyclonal or monoclonal antibodies. Such antibodies can be used not only for diagnostic purposes but also for the preparation of antibody columns with which it is possible to separate PP15 from solutions which contain it together with other proteins.

It is also possible using the cDNA, or parts thereof, to isolate in a straightforward manner from a genomic bank the genomic clone which codes for PP15 and which not only facilitates the expression in eukaryotic cells but also allows further diagnostic conclusions to be drawn.

The invention is further defined in the patent claims and is explained in detail in the Examples which follow.

The following abbreviations are used, apart from those explained in the text:

EDTA=sodium ethylenediaminetetraacetate
SDS=sodium dodecyl sulfate
DTT=dithiothreitol
BSA=bovine serum albumin

EXAMPLES

1. Isolation of RNA from human placenta

RNA was obtained from mature human placenta (method of Chirgwin et al., Biochemistry 18 (1979) 5294-5299). About 10 g of placental tissue were ground in liquid nitrogen in a mortar, suspended in 80 ml of 4M guanidinium thiocyanate containing 0.1M mercaptoethanol, and treated in a homogenizer (Ultraturrax) at 20,000 rpm for 90 sec. The lystate was centrifuged (Sorvall GSA rotor) at 7,000 rpm for 15 min, and the supernatant was precipitated with 2 ml of 1M acetic acid and 60 ml of abs. ethanol at −20° C. overnight. The nucleic acids were sedimented at 6,000 rpm and −10° C. for 10 min and then completely dissolved in 40 ml of 7.5M guanidinium hydrochloride (pH 7.0) and precipitated with a mixture of 1 ml of 1M acetic acid and 20 ml of abs. ethanol. To remove the DNA, the precipitation was repeated once more with each of the volumes being halved. The RNA was dissolved in 12 ml of H$_2$O, precipitated with a mixture of 1.2 ml of 4M potassium acetate and 24 ml of abs. ethanol sedimented and, finally, again taken up in 10 ml of H$_2$O (1 ml per g of tissue).

2. Obtaining poly(A)-containing placental mRNA

To obtain poly(A)-containing mRNA, the placental RNA was fractionated by oligo(dT)-cellulose chromatography (Aviv and Leder, Proc. Natl. Acad. Sci. U.S.A. 69 (1973) 1408-1412) in 2 ml Pasteur pipettes in LiCl. About 5 mg of placental RNA in buffer 1 (500 mM LiCl, 20 mM Tris (pH 7.5), 1 mM EDTA, 0.1% SDS) were applied to the column. Whereas the poly(A)+ RNA was bound to oligo(dT)-cellulose, it was possible to elute the poly(A)− RNA again. After a washing step with buffer 2 (100 mM LiCl, 29 mM Tris (PH 7.5), 1 mM EDTA, 0.1% SDS), the poly(A)+ RNA (placental mRNA) was eluted from the column with buffer 3 (5 mM Tris (pH 7.5), 1 mM EDTA, 0.05% SDS).

For further purification, the poly(A)+ RNA was adjusted to buffer 1 and again chromatographed on oligo(dT)-cellulose. The yield of placental poly(A)+ RNA after this second purification step was about 4% of the RNA used.

3. Synthesis of cDNA from human placental (placental cDNA) and double-stranded cDNA (dsDNA)

The integrity of the poly(A)-containing placental mRNA was checked in a 1.5% agarose gel before the cDNA synthesis.

Then 4 μg of placental mRNA were dissolved in 65.5 μl of H$_2$O, denatured at 70° C. for 10 min and cooled in ice. The cDNA was synthesized in a 100 μl mixture after addition of 20 μl of RT$_1$ buffer (250 mM Tris (pH 8.2) at 42° C., 250 mM KCl, 30 mM MgCl$_2$), 2.5 μl of 20 mM dNTP (i.e. all four deoxynucleoside triphosphates), 1 μl of oligo(dT) of 1 μg/ml, 1 μl of 1M DTT, 2 μl of RNAsin (Boehringer Mannheim) and 8 μl of reverse transcriptase (24 U/μl Boehringer Mannheim) at 42° C. for 90 min. Double-stranded cDNA (dsDNA) was synthesized by the method of Gubler and Hoffmann (Gene 25 (1983) 263-269). The synthesis was carried out immediately after the cDNA synthesis by addition of 305.5 μl of H$_2$O, 80 μl of RT$_2$ buffer (100 mM Tris (pH 7.5), 25 mM MgCl$_2$, 500 mM KCl, 50 mM DTT, 250 μg/ml BSA), 2 μl of RNase H (2 U/μl), 2.5 μl of E. coli DNA ligase (5 U/μl), 5 μl of 15 mM β-NAD, and 5 μl of DNA polymerase I (5 U/μl) and incubation at 15° C. for 5 h. The reaction was stopped by heat inactivation (70° C., 30 min).

After addition of 55 μl of 250 μM dNTP, 55 μl of 10 mM Tris (pH 7.5), 10 mM MgCl$_2$, 10 μg/ml BSA, 3 μl of T4 DNA polymerase I (1 U/μl), 2 μl of RNase H (2 U/μl) and 2 μl of RNase A (2 μg/ml) to the reaction mixture it was incubated at 37° C. for a further 13 min in order to ensure that the synthesis on the second DNA strand was complete ("repair reaction").

4. Ligation of EcoRI linkers to the dsDNA, and opening of the linkers

To set up a placental cDNA bank, the dsDNA was provided with EcoRI ends in order to be able to ligate it into the EcoRI cleavage site of the phage vector λgt10 (T. Maniatis et al. (1982), Molecular Cloning, A Laboratory Manual, Cold Spring Harbor). For this purpose, the dsDNA was a) treated with EcoRI methylase in order to protect internal EcoRI cleavage sites of the dsDNA, and b) provided with EcoRI linkers which c) were then opened with EcoRI.

Re a):

The methylase reaction of dsDNA was carried out directly following the repair reaction after addition of 25 μl of 500 mM EDTA (pH 8.0), 60 μl of methylase buffer (100 mM NaOAc (pH 5.2), 2 mg of S-adenosyl-L-methionine) and 2 μl of EcoRI methylase (20 U/μl) by incubation at 37° C. for 30 min.

The reaction mixture was extracted with phenol, and the dsDNA was precipitated with 60 μl of 4M NaOAc and 1300 μl of ethanol. The dsDNA was washed twice with 70% ethanol, extracted by shaking once with ether, and dried.

Re b):

The EcoRI-methylated dsDNA was dissolved in 88 μl of H$_2$O and after addition of 10 μl of ligase buffer (500 mM Tris (pH 7.4), 100 mM MgCl$_2$, 100 mM DTT, 100 mM spermidine, 10 mM ATP, 1 mg/ml BSA) and 1 μl of T4 DNA ligase (10 U/μl), was ligated with 1 μl of EcoRI linkers (0.5 μg/μl) (pGG-AATTCC and pA-GAATTCT) at 15° C. overnight.

Re c):

The volume of the ligase mixture was made up to 120 μl with 6 μl of H$_2$O, 12 μl of 10×EcoRI buffer and 2 μl of EcoRI (120 U/μl). The EcoRI digestion was carried out at 37° C. for 2 h.

5. Removal of unbound linkers on a potassium acetate gradient, and selection of the dsDNA for size All unbound EcoRI linkers were removed from the dsDNA by applying the EcoRI reaction mixture in toto to a potassium acetate gradient (5-20% KOAc, 1 mM EDTA, 1 μl/ml ethidium bromide) and centrifuging (Beckman SW 65 rotor) at 50,000 rpm and 20° C. for 3 h. The gradient was fractionated from below in such a way that the first five fractions measured 500 μl, and all the remainders measured 100 μl. The fractions were precipitated with 0.01 volume of acrylamide (2 mg/ml) and 2.5 volumes of ethanol, washed once with 70% strength ethanol and dried, and each was taken up in 5 μl of H$_2$O.

To determine the size of the dsDNA, 1 μl of each fraction was analyzed in a 1.5% agarose gel. In addition, the quantity of dsDNA was determined using 1 μl of each fraction.

Fractions containing dsDNA above 500 bp were combined, and the sample was concentrated until the final concentration was 27 μl/ml.

6. Insertion of the dsDNA into the phage vector λgt10, and in vitro packaging reaction The dsDNA was inserted into the EcoRI cleavage site of the phage vector λgt10 (Vector Cloning Systems, San Diego, Calif.) in a 4 μl ligase mixture: 2 μl of dsDNA, 1 μl of λgt10×EcoRI (1 μg/ml), 0.4 μl of ligase buffer, 0.5 μl of H$_2$O, 0.1 μl of T4 DNA ligase. The mixture was incubated at 15° C. for 4 h.

To establish the placental cDNA bank in the phage vector λgt10, the ligase mixture was subsequently subjected to an in vitro packaging reaction with the λ-lysogenic cell extracts E. coli NS 428 and NS 433 at room temperature for 2 h (Vector Cloning Systems, San Diego, Calif.; Enquist And Sternberg, Methods in Enzymology 68, (1979), 281-298). The reaction was stopped with 500 μl of suspending medium (SM: 0.1M NaCl, 8 mM MgSO$_4$, 50 mM Tris (pH 7.5), 0.01% gelatin) and 2 drops of chloroform.

7. Titer determination and analysis of the placental cDNA bank

The number of plaque-forming units (PFU) of the placental cDNA bank were determined using competent cells of E. coli K 12 strain C600 HFL: it was $1 \times 10^6$ PFU.

8. Oligonucleotide probes for screening the placental cDNA bank

Oligonucleotide probes (PP15 oligonucleotide 103 and 140) and a pool of oligonucleotides (PP15 oligonucleotide pool 139) were synthesized for the analysis of the placental cDNA bank. Their sequences were derived from the amino acid sequence of three cyanogen bromide fragments of PP15.

The manner of construction and the use of the probes essentially followed the rules of R. Lathe, loc. cit.

The oligonucleotide sequences were labeled at the 5' end using T4 polynucelotide kinase in the presence of (λ-$^{32}$P) ATP (using 60 μCi/40 μl of reaction mixture). The probes had a specific activity of $1 \times 10^8$ Bq/μl or $1.5 \times 10^6$ Bq/pmol.

9. Screening of the placental cDNA with PP15-specific oligonucleotides $1 \times 10^6$ PFU of the placental cDNA bank were examined with the PP15 oligonucleotide probes 103, 140 and 139 together. For this purpose, $3 \times 10^4$ PFU were plated out with cells of the E. coli K 12 strain C 600 HFL in soft agar on 13.5 cm Petri dishes and incubated at 37° C. for 6 h. Lysis was still incomplete at this time. The plates were incubated in a refrigerator overnight, and the phages were transferred to nitrocellulose filters (Schleicher and Schull, BA 85, Ref. No. 401124) (duplicates). The nitrocellulose filters and Petri dishes were marked with an injection needle to allow later assignment of positive plaques. During the processing of the nitrocellulose filters, the Petri dishes were stored in a cold room. The DNA on the nitrocellulose filters was denatured by placing the filters on filter paper (Whatman M3) impregnated with 1.5M NaCl, 0.5M NaOH for 5 min. The filters were then renatured in the same way using 1.5M NaCl, 0.5M Tris (pH 8.0) and washed with 2×SSPE (0.36M NaCl, 16 mM NaOH, 20 mM NaH$_2$PO$_4$, 2 mM EDTA). The filters were then dried in vacuo at 80° C. for 2 h. The filters were washed in 3×SSC, 0.1% SDS (20×SSC=3M NaCl, 0.3M Na citrate) at 65° C. for 4 h and prehybridized at 65° C. for 4 h (prehybridization solution: 0.6M NaCl, 0.06M Tris (pH 8.3), 6 mM EDTA, 0.2% non-ionic synthetic sucrose polymer ($^R$Ficoll), 0.2% polyvinylpyrrolidone 40, 0.2% BSA, 0.1% SDS, 50 μg/ml denatured herring sperm DNA). The filters were incubated overnight with the addition of 100,000-200,000 Bq of the labeled oligonucleotide per ml of hybridization solution (as prehybridization solution but without herring sperm DNA) in beakers or in sealed polyethylene films, shaking gently. The hybridization temperature was 46° C. for oligonucleotide probe 139 and 52° C. for the other probes. The nitro-cellulose filters were washed with 6×SSC, 0.05M sodium pyrophosphate at room temperature for one hour and at the relevant hybridization temperature for a further hour. The filters were dried and autoradiographed overnight. Signals which appeared on both duplicates of the X-ray film were assigned to the Petri dishes, and the region (about 50 plaques) was punched out with the wide end of a Pasteur pipette, and the phages were resuspended in 1 ml of SM buffer. Positive phages were singled out over three cycles until a single clone was obtained.

Three samples each of 1×10⁶ PFU of the placental cDNA bank were examined. Not until the third screening were 2 signals identified on duplicate filters. The two clones PP15-24 and PP15-28 contain the complete cDNA of PP15.

Tab. 1 compares the oligonucleotide sequences 103, 139 and 140 with the PP15 sequence found.

```
                                    Met Gly Asp
5'... CGCTCCAGA ATG GGA GAC ... 3'
```

Since there is no NcoI site at the ATG, it is impossible for this DNA to be cloned directly into the pTrc99A expression vector. However, an NcoI site can be achieved by mutagenesis, by two base-exchanges in the PP15 sequence: 5' GAATGG 3' to 5' CCATGG 3'. The second amino acid (Gly) is unaffected by this manipulation, because the second codon of the PP15 structural sequence starts with a "G". For the mutagenesis, an EcoRI fragment 902 base-pairs in size was isolated from the PP15 cDNA clone PP15-28 and ligated into the mutagenesis vector pMa5-8 (FIG. 1) which had likewise been cut with EcoRI and had been dephosphorylated. The resulting plasmid pMa5-8-PP15 (with

TABLE 1

PP15 sequence vs. PP15 oligonucleotide 103

```
301 ATCACCGCGCAGGACCATCAGCCCACTCCAGATAGCTGCATCATCAGCAT 350
  1 ................................................AT   2

351 GGTTGTGGGCCAGCTTAAGGCGGATGAAGACCCCATCATGGGGTTCCACC  400
  3 GGTGGTGGGCCAGCTGAAGGCTGATGAGGACCCC.................  36
```

PP15 sequence vs. PP15 oligonucleotide 139

```
401 AGATGTTCCTATTAAAGAACATCAACGATGCTTGGGTTTGCACCAATGAC  450
  1 ................AAGAACATCAACGATGCCTGGAC............   23
```

PP15 sequence vs. PP15 oligonucleotide 140

```
151 TACTACCAGTTATTTGATAATGATAGAACCCAACTAGGCGCAATTTACAT  200
  1 ............TTTGACAATGACCGGACCCAGCTGGGCGCCATCTACAT   38

201 TGACGCGTCATGCCTTACGTGGGAAGGACAACAGTTCCAGGGGAAAGCTG  250
 39 TGATGC............................................   44
``` the correct orientation of the PP15 EcoRI insert in relation to F1-ori) was then subjected to the gapped duplex mutagenesis protocol (Kramer et al. (1984) Nucl. Acids. Res. 12, 9941-9456), using the following oligodeoxynucleotide:

10. DNA sequence analysis

The phage clones PP15-24 and PP15-28 were propagated, and the DNA of each of them was extracted. In each case the EcoRI fragment was isolated and ligated into the EcoRI site of the Bluescript M13 vector (Stratagene, San Diego, Calif., U.S.A.) for restriction analyses and sequence analyses using the enzymatic dideoxy method of Sanger. The sequence shows an open reading frame and codes for a protein having a maximum of 127 amino acids. PP15 has a calculated molecular weight of 14478 d (including methionine), which agrees well with the figure, mentioned in the introduction, from the Patent DE-A 2,952,792.

11. Expression of the immunosuppressive protein PP15

The vector pTrc99A (E. Amann et al. (1988) Gene 69, 301-315) was used to express the non-fused mature PP15 protein in E. coli. The DNA sequence of the PP15 cDNA at the initiation codon is as follows:

```
5' GGCTTGTCTCCCATGGTGGAGCGTCAC 3'
```

One clone which had the desired mutation was identified by restriction analysis and was called pMc5-8PP15-NcoI. The NcoI-EcoRI fragment 798 base-pairs in size was isolated from this plasmid and ligated into the correspondingly cut pTrc99A vector. The resulting plasmid pTrc-99A-PP15 embraces 4918 base-pairs and, after induction of the trc promoter, expresses the non-fused PP15 protein about 15 kD in size.

We claim:

1. An isolated DNA or RNA which (a) encodes the protein PP15 having the amino acid sequence shown in FIG. 2; and (b) hybridizes with the DNA having the sequence shown in FIG. 2, under stringent conditions.

2. Vectors containing a DNA as claimed in claim 1.

3. A transformed cell containing DNA as claimed in claim 2.

* * * * *